(12) United States Patent
Stroud et al.

(10) Patent No.: US 11,359,103 B2
(45) Date of Patent: Jun. 14, 2022

(54) SCRUB-RESISTANT INK AND METHODS AND APPARATUS FOR FABRICATION AND USE THEREOF

(75) Inventors: Eric Stroud, Oak Ridge, NJ (US); Gary J. Pieringer, Shrewsbury, NJ (US)

(73) Assignee: VISCOT MEDICAL, LLC, East Hanover, NJ (US)

(*) Notice: Subject to any disclaimer, the term of this patent is extended or adjusted under 35 U.S.C. 154(b) by 1855 days.

(21) Appl. No.: 12/613,813

(22) Filed: Nov. 6, 2009

(65) Prior Publication Data
US 2010/0121343 A1    May 13, 2010

Related U.S. Application Data

(60) Provisional application No. 61/112,212, filed on Nov. 7, 2008.

(51) Int. Cl.
*C09D 11/16* (2014.01)
*A61B 17/00* (2006.01)
(Continued)

(52) U.S. Cl.
CPC .......... *C09D 11/16* (2013.01); *B43K 5/02* (2013.01); *C09D 11/17* (2013.01); *A61B 2090/395* (2016.02)

(58) Field of Classification Search
CPC .... A61B 2019/545; C09D 11/16; C09D 11/17
(Continued)

(56) References Cited

U.S. PATENT DOCUMENTS 3,551,554 A    12/1970  Herschler
3,617,185 A *  11/1971  Drautz ............... C09B 67/0076
                                                      8/527
(Continued)

FOREIGN PATENT DOCUMENTS

CN          1982381 A      6/2007
JP        S 56129274 A    10/1981
(Continued)

OTHER PUBLICATIONS

International Search Report and Written Opinion dated Jun. 22, 2010 for PCT Application No. PCT/US2009/063582.
(Continued)

*Primary Examiner* — Shuangyi Abu Ali
(74) *Attorney, Agent, or Firm* — Moser Taboada

(57) ABSTRACT

Scrub resistant inks and methods and apparatus for fabrication and use thereof are provided. Scrub-resistant ink compositions may include a dye for marking skin; and a solvent dissolving a marking effective amount of the dye, wherein the solvent comprises about 0.1 to about 90 percent of a polar aprotic solvent. Apparatus for marking patients may include an ink reservoir; an ink dispenser having a fluid connection to the ink reservoir to dispense the ink at a desired rate to mark a patient; and a scrub resistant ink disposed in the ink reservoir. Methods for forming scrub-resistant ink compositions may include providing a marking effective amount of a dye suitable for use in marking skin; and mixing the dye with a first solvent comprising 0.1% to 90% of a polar aprotic solvent. Methods of marking patients may include applying an ink as recited above to a body part of the patient.

17 Claims, 2 Drawing Sheets

(51) Int. Cl.
*C09D 11/17* (2014.01)
*B43K 5/02* (2006.01)
*A61B 90/00* (2016.01)

(58) Field of Classification Search
USPC ...................................................... 106/31.13
See application file for complete search history.

(56) References Cited

U.S. PATENT DOCUMENTS

| | | | |
|---|---|---|---|
| 4,500,321 A * | 2/1985 | Hugelshofer | C09B 67/0073 8/527 |
| 4,572,831 A | 2/1986 | Rosen | |
| 5,507,865 A * | 4/1996 | Yoshida et al. | 106/31.43 |
| 5,626,634 A * | 5/1997 | Goldmann | C09B 67/0046 8/527 |
| 5,713,890 A | 2/1998 | Chasan | |
| 6,056,737 A | 5/2000 | Rosen | |
| 6,264,731 B1 | 7/2001 | Gundlach et al. | |
| 6,541,538 B1 * | 4/2003 | Matzinger | C08F 226/10 523/160 |
| 6,814,760 B2 | 11/2004 | Anderson et al. | |
| 2003/0113540 A1 | 6/2003 | Anderson et al. | |
| 2003/0119943 A1 | 6/2003 | Tucker et al. | |
| 2003/0150355 A1 | 8/2003 | Choy et al. | |
| 2004/0118320 A1 * | 6/2004 | Akers | C09D 11/32 106/31.6 |
| 2004/0236211 A1 | 11/2004 | Burbank et al. | |
| 2005/0011404 A1 * | 1/2005 | Patel et al. | 106/31.27 |
| 2005/0178288 A1 * | 8/2005 | Taguchi | 106/31.13 |
| 2005/0237483 A1 | 10/2005 | Phelan | |
| 2007/0203504 A1 | 8/2007 | Denny et al. | |

FOREIGN PATENT DOCUMENTS

| | | |
|---|---|---|
| JP | H 03103483 A | 4/1991 |
| KR | 20040045158 A | 6/2004 |

OTHER PUBLICATIONS

Declaration of Mark Kaforey, Vice President of Xodus Medical Inc. executed Feb. 3, 2012 (NHL-XOD-06 declaration).
Declaration of Craig Kaforey, President of Xodus Medical Inc. executed Feb. 3, 2012 (NHL-XOD-06 declaration).
Invoice No. 32884 of Xodus Medical Inc. to Owens & Minor #89 in the amount of $200.00 dated Dec. 4, 2006.
Invoice No. 33033 of Xodus Medical Inc.to Owens & Minor #79 in the amount of $587.00 dated Dec. 12, 2006.
Invoice No. 05WFA1424561 of Shanghai Lansheng Footwear Corporation to Xodus Medical Inc. in the amount of $44475.38 dated Jan. 7, 2005.
Vernon, Halfbakery: Ink-Jet Tattoos, Apr. 11, 2005, p. 1 of 3, www.halfbakery.com.
Allergie/Ausschlag nach Henna-Tattoo, Meinungen zu Gesundeit & Medizin Forum HolidayCheck, Allergy/rash after henna tattoo, Apr. 29, 2022, pp. 1-6.

* cited by examiner

SCRUB-RESISTANT INK AND METHODS AND APPARATUS FOR FABRICATION AND USE THEREOF

CROSS-REFERENCE TO RELATED APPLICATIONS

This application claims benefit of U.S. provisional patent application Ser. No. 61/112,212, filed Nov. 7, 2008, which is herein incorporated by reference.

FIELD

Embodiments of the present invention generally relate to inks, pens, and methods for patient marking.

BACKGROUND

In marking patients for surgery, such as to indicate the correct site of the patient to operated upon, it is desirable that the ink used not be readily scrubbed off with surgical disinfectants, such as chlorhexidine, benzalkonium chloride, povidone-iodine, or the like. Conventional marking inks often become substantially smeared and/or faint after a short time (e.g., about ten seconds or less) of scrubbing with a surgical disinfectant.

Thus, there is a need for an improved ink for marking patients prior to surgery.

SUMMARY

Scrub-resistant inks and methods of fabrication and use are provided herein. In some embodiments, a scrub-resistant ink composition may include a dye for marking skin; and a solvent dissolving a marking effective amount of the dye, wherein the solvent comprises about 0.1 to about 90 percent of a polar aprotic solvent.

In some embodiments, an apparatus for marking patients may include an ink reservoir; an ink dispenser having a fluid connection to the ink reservoir to dispense the ink at a desired rate to mark a patient; and a scrub-resistant ink disposed in the ink reservoir. The scrub-resistant ink may be a scrub-resistant ink as taught in any of embodiments disclosed herein.

In some embodiments, a method for forming a scrub-resistant ink composition may include providing a marking effective amount of a dye suitable for use in marking skin; and mixing the dye with a first solvent comprising 0.1% to 90% of a polar aprotic solvent. In some embodiments, a method of forming an ink may include mixing a marking effective amount of dye with a first solvent to form a dye concentrate; and mixing the dye concentrate with a second solvent to form the ink.

In some embodiments, a method of making a scrub-resistant ink may include providing a pre-existing ink; mixing a polar aprotic solvent into the pre-existing ink; and forming an ink mixture having a resultant solvent comprising 0.1% to 90% polar aprotic solvent.

In some embodiments, the polar aprotic solvent comprises dimethyl sulfoxide (DMSO). In some embodiments, the dye comprises Gentian violet. The ink may be scrub-resistant (e.g., the mark remains visible for 10 seconds or longer, for 20 seconds or longer, or for 30 seconds or longer, of scrubbing, as discussed below).

In some embodiments, a method of marking a patient (e.g., a human or an animal), such as prior to or during a surgical procedure, may include determining a portion of a patient to be marked, and applying a scrub-resistant ink to the patient to mark the portion of the patient. The scrub-resistant ink may be a scrub-resistant ink as taught in any of embodiments disclosed herein. Other embodiments of the present invention are described in the detailed description, below.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Figure 1A:
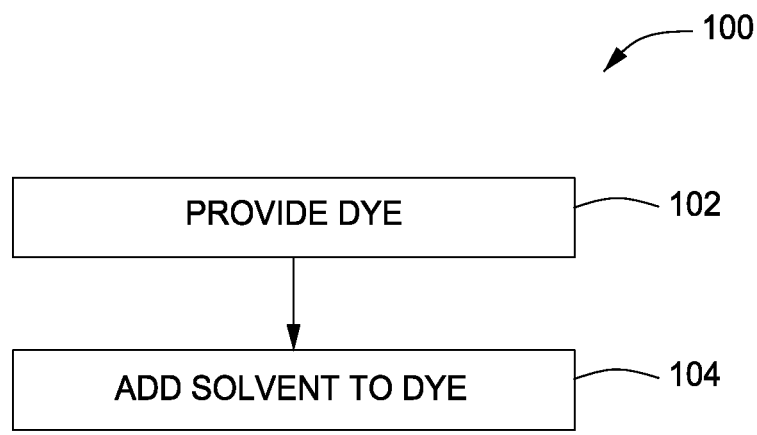
FIGS. 1A and 1B depict flow charts of methods for making scrub-resistant ink in accordance with some embodiments of the present invention.

To facilitate understanding, identical reference numerals have been used, where possible, to designate identical elements that are common to the figures. The figures are not drawn to scale and may be simplified for clarity. It is contemplated that elements and features of one embodiment may be beneficially incorporated in other embodiments without further recitation.

DETAILED DESCRIPTION

Embodiments of the present invention provide ink compositions, pens, and methods for marking surgical patients, and for other uses needing a scrub-resistant ink. The ink composition comprises a dye, such as Gentian violet, and a polar aprotic solvent, such as dimethyl sulfoxide (DMSO).

FIG. 1A describes one embodiment of a method 100 for producing an ink composition in accordance with some embodiments of the present invention. The method 100 generally begins at 102 where a dye is provided. The dye may comprise hexamethyl pararosaniline chloride or any hexamethyl pararosaniline salt retaining substantially the color of the chloride. The hexamethyl pararosaniline chloride is also known as Gentian violet, Andergon, Aniline violet, Axuris, Badil, Basic Violet 3, Brilliant Violet 58, crystal violet, Gentiaverm, Hexamethyl-p-rosaniline chloride, Meroxylan, Meroxyl, Methylrosanilide chloride, Methyl Violet 10B, Methyl Violet 10BNS, Pyoktanin, Vianin, Viocid, or Viola Crystallina.

The dye may generally be provided in an amount that provides effective marking (e.g., an effective amount). By "effective amount" in this context it is meant that, in a given ink composition according to the invention, one could remove all other dyes (other than Gentian violet) and the composition would still provide legible marking.

For example, the concentration of the dye (e.g., Gentian violet) can be, for example, from 0.1 percent or more, 1 percent or more, 10 percent or more, or 50 percent or more. Unless otherwise noted, percent amounts in this specification are w/w percentages. The concentration of the dye (e.g., Gentian violet) can be, for example, from 5 percent or less, 25 percent or less, 50 percent or less, 75 percent or less, or saturation or less. The amount of dye can also be above saturation in the carrier solvent, such that some solid dye (e.g., Gentian violet crystals) may form in the composition. Typically, the concentration of the dye is a concentration that provides useful skin marking as described herein. In some embodiments, the concentration of the dye is between about 20 percent to about 40 percent of the ink composition. In some embodiments, the concentration of the dye is between about 25 percent to about 35 percent of the ink composition.

Next, at 104, a solvent may be added to the dye. The solvent may be a polar aprotic solvent. Polar aprotic solvents are solvents that do not exchange protons (acidic hydrogens) with a substance dissolved in it. Examples include dimethyl sulfoxide, dimethylformamide, hexamethylphosphoramide, dioxane, tetrahydrofuran, dimethylacetamide, and N-methyl-2-pyrroidone. In some embodiments, DMSO is used as the solvent, which advantageously provides much lower in-vivo toxicity than other polar aprotics. In addition, DMSO transverses the skin quite readily. Aprotics are able to dissolve both polar and nonpolar chemical compounds, making them useful for dye formulations. For example, certain dyes have low water solubility and the aprotic solvent aids in increasing solubility.

In some embodiments, the dyes are dissolved in a solution containing about 0.1% to about 90% of the polar aprotic solvent, such as dimethyl sulfoxide (DMSO). For example, in some embodiments, the dissolving solution contains about 1% or more polar aprotic solvent (such as DMSO), or 2% or more, 5% or more, or 10% or more, or 20% or more, 25% or more, or 30% or more, or 35% or more, or 40% or more, or 45% or more, 50% or more, 60% or more, 70% or more, or 80% or more. In some embodiments, the dissolving solution contains about 90% or less polar aprotic solvent (such as DMSO), or 85% or less, or 80% or less, or 75% or less, or 70% or less, 65% or less, or 60% or less, or 55% or less, 50% or less, or 45% or less, or 40% or less, or 35% or less, or 30% or less, 25% or less, or 20% or less.

In some embodiments, the dyes are dissolved in a solution containing about 50% to about 90% of the polar aprotic solvent. In some embodiments, the dyes are dissolved in a solution containing about 60% to about 65% of the polar aprotic solvent.

The residue, or balance, of the ink composition may comprise water, a water-miscible alcohol, a water-miscible glycol ether, a thickener, a fragrance, or combinations thereof. Suitable water miscible alcohols may include C1 to C6 alcohols, for example, ethanol, n-propanol, 2-propanol, or the like. Certain glycol ethers enhance penetration through the skin, further enhancing the scrub resistance if the ink composition. Glycol ethers have similar salvation powers of alcohols, but with much higher boiling points. For example, flammability issues are abated when glycol ethers are substituted for primary alcohols in dye formulations. Ethoxydiglycol (diethylene glycol monoethyl ether), is a preferable glycol ether because of its low toxicity. Ethoxydiglycol is typically used in cosmetic formulations under the trade name Transcutol®.

In some embodiments, the balance of the ink composition is no more than about 20 percent of the ink composition. In some embodiments, the balance of the solution may be no more than 5%, or 3%, or 2%, or 1%, or 0.5% of the ink composition.

The dye and solvent may be mixed, for example, by stirring, swirling, shaking, blending, or the like, to homogenize the mixture and form the ink. The solvent can be warmed to facilitate the dissolution of the dye. However, elevating the temperature to above 70° C. for a sustained period of time may degrade the dye. Of course, such decomposition will depend on the solvent composition, and the length of exposure to detrimentally elevated temperature. In some embodiments, any water in the composition may be first added to the polar aprotic solvent, such as DMSO, which results in an exothermic reaction. For example, in some embodiments, the vessel containing the solution may be heated to a temperature of between about 70 to 80 degrees Celsius. The solution can then be cooled, for example, to about room temperature, prior to adding the dye, to prevent any thermal degradation of the dye.

Thus, a scrub-resistant ink comprising a dye mixed in a polar aprotic solvent may be produced. Using a polar aprotic solvent, such as DMSO, to solvate the dye advantageously facilitates incorporation of more dye into solution for the ink composition. The ink may generally have a composition as discussed above. In one specific example, the ink may comprise about 60-63% of the polar aprotic solvent (e.g., DMSO), about 30% of the dye (e.g., Gentian violet), with the balance being substantially water.

Figure 1B:
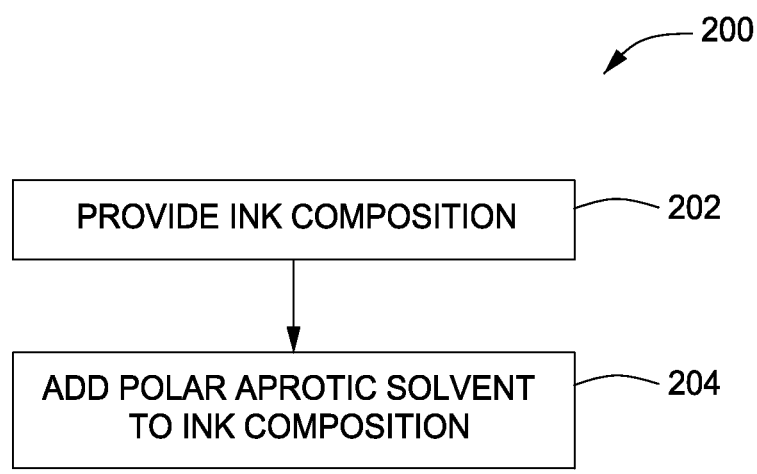

In some embodiments, a method of making a scrub-resistance ink may include providing a pre-existing ink composition and adding a solvent as discussed above to enhance wear characteristics of the ink. For example, a method 200 of producing a scrub-resistant ink is depicted in FIG. 1B. The method 200 may generally begin at 202 where a pre-existing ink composition may be provided. The pre-existing ink composition may generally be any commercially available surgical skin marking ink.

Next, at 204, a polar aprotic solvent, such as DMSO, may be added to the ink composition. In certain embodiments, such solvent comprises up to about 40 percent of the resultant composition (with the balance being the pre-existing ink composition). In some embodiments, the resultant composition may comprise about 1.5 to about 40 percent polar aprotic solvent. In some embodiments, the resultant composition may comprise about 20 to about 40 percent polar aprotic solvent. In some embodiments, the resultant composition may comprise about 25 to about 30 percent polar aprotic solvent. In some embodiments, the resultant composition may comprise about 25 percent polar aprotic solvent.

To make the scrub-resistant ink from the pre-existing ink described above (or to make such ink more scrub resistant), one can add the solvent at room temperature or warmed to facilitate keeping the dye in solution while the resultant solvent equilibrates. Limits on such warming shall be dependent on the particular dye(s) used in the ink. The polar aprotic solvent, such as DMSO, may be added slowly to the pre-existing ink to limit exothermic reactions with any water present in the pre-existing ink.

The scrub-resistance of an ink of the invention or made according to the invention can be tested by marking skin with the ink and scrubbing with a vigorousness appropriate for pre-surgical preparation with a 2 percent w/w solution of chlorhexidine in 70 percent by volume isopropyl alcohol. The ink is scrub-resistant if it resists smearing and/or fading for 10 seconds or longer. Preferably, the inks according to the invention resist smearing and/or fading for substantially longer, such as 20 sec or more, or 25 sec or more, or 30 sec or more.

Further provided is a pen containing and for delivering the ink. The pen can be any suitable pen for holding and delivering the ink, such as, for example a felt pen. Such a pen will typically have a reservoir connected by a felt-filled channel to the felt tip. "Felt" refers to any porous fabric suitable for dispensing and spreading the ink and resistant to the solvent. While a felt pen is often useful for marking skin, any pen structure may be used. For example, ball-point or rollerball pens, pens with nibs (e.g., fountain pens), and the like can be used. Although a pen is provided as an example of providing the ink, any suitable delivery mechanism may be utilized to hold and/or deliver the scrub-resistant inks of the present invention.

Figure 2:
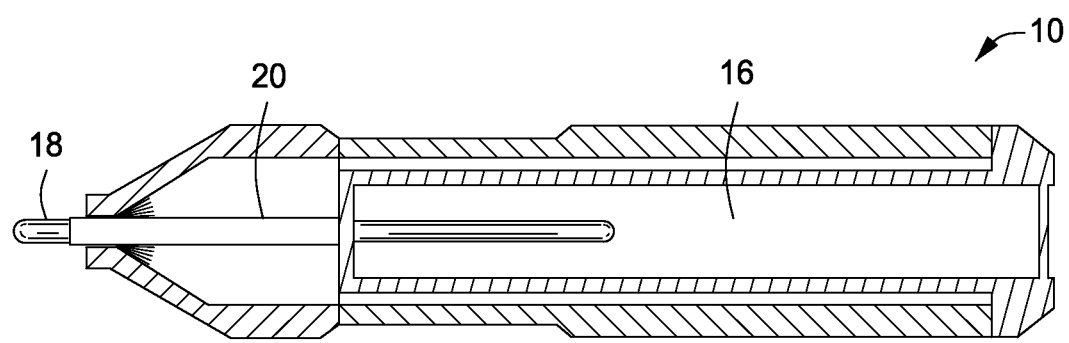
FIG. 2 depicts a pen for marking an animal in accordance with some embodiments of the present invention.

For example, FIG. 2 depicts an illustrative pen 10 for marking a patient, such as a human or other animal. The pen 10 includes a reservoir 16, dispenser 18 (such as felt) for dispensing ink, and conduit 20 for fluid connection to the reservoir 16. The pen shown in FIG. 2 is illustrative only, and any other marking instrument suitable for us in marking a patient with scrub-resistant inks as taught herein may be utilized.

Figure 3:
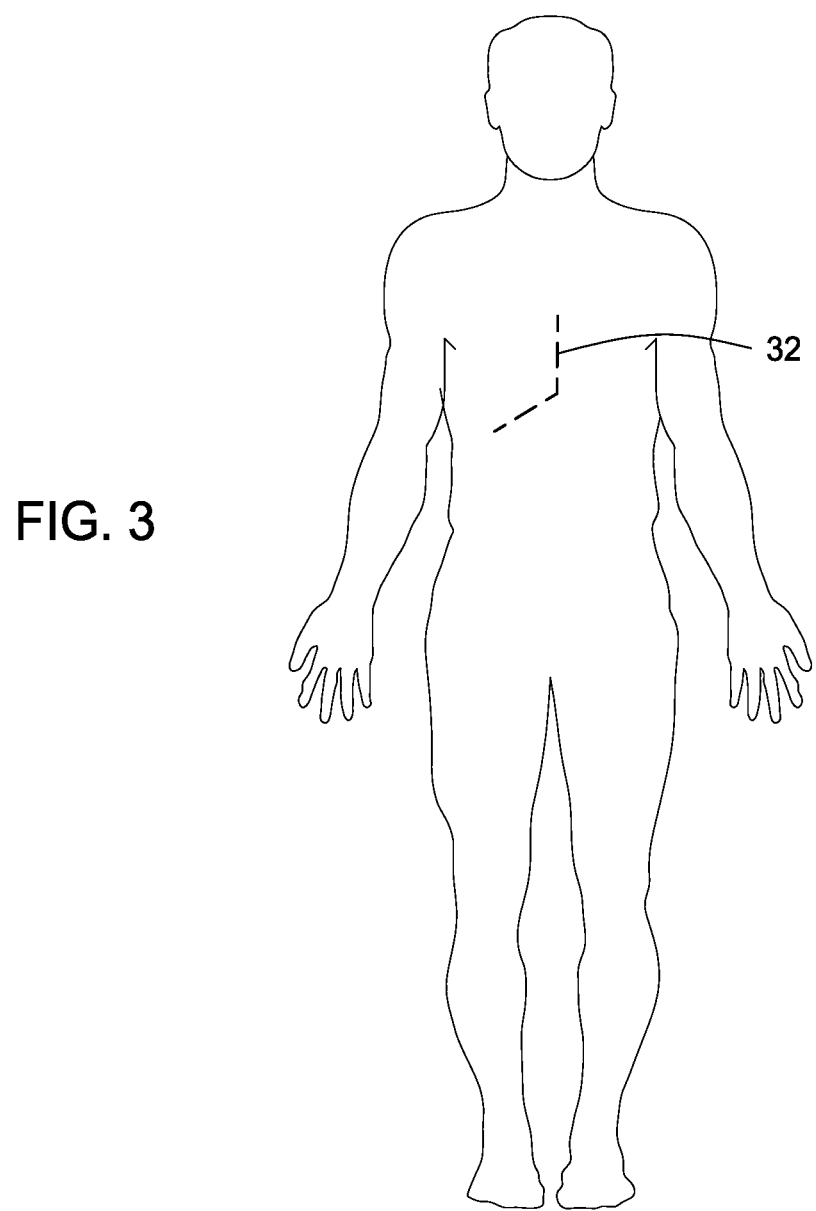
FIG. 3 illustrates a patient having markings made thereon in accordance with some embodiments of the present invention.

The inks can be used, for example, to mark the correct site or other body part to be operated upon. It can be used to mark the incision points and lines. Such markings are useful in error prevention protocols, such as a verbal check list answered by the professionals involved in a surgical operation. As illustrated in FIG. 3, a prospective course of incisions may be traced with dashed line 32.

Other uses of the scrub-resistant ink should be apparent. These include markings to establish that one has voted, paid a cover charge, or the like. Animals can be marked to distinguish them or help trace their sourcing, or the like. The inks can also be used to provide sustained, but nonpermanent, skin decoration.

Thus, methods, compositions and devices have been provided herein that provide improved skin marking. Such skin marking advantageously has increased wear or scrub resistance as compared to conventional inks for marking skin.

While the foregoing is directed to embodiments of the present invention, other and further embodiments of the invention may be devised without departing from the basic scope thereof.

The invention claimed is:

1. A scrub-resistant ink composition, comprising:
a dye for marking skin; and
aqueous solvent dissolving all of the dye, wherein the solvent comprises 50 to 90 percent by weight of polar aprotic solvent(s), wherein the amount of dye is between 1 percent to 5 percent by weight of the composition, and wherein the composition is free of thickeners, wherein the composition is entirely a solution, and wherein polar aprotic solvent, water and dye comprise 95% by weight or more of the ink composition.

2. The ink composition of claim 1, wherein the ink composition is scrub-resistant such that a mark made on skin of a patient remains visible after 30 seconds or longer of scrubbing with a vigorousness appropriate for pre-surgical preparation with a 2 percent w/w solution of chlorhexidine in 70 percent by volume isopropyl alcohol.

3. The ink composition of claim 1, wherein the dye comprises Gentian violet.

4. The ink composition of claim 1, wherein the polar aprotic solvent consists of dimethyl sulfoxide (DMSO).

5. The ink composition of claim 1, wherein the solvent comprises about 60% to about 65% of the polar aprotic solvent.

6. The ink composition of claim 1, wherein the ink composition consists of the dye, the polar aprotic solvent, water, and, if present, any further ingredients are limited to one or more of water-miscible alcohol, water-miscible glycol ether and fragrance.

7. A marking pen for marking patients, comprising:
an ink reservoir;
an ink dispenser having a fluid connection to the ink reservoir to dispense the ink at a desired rate to mark a patient; and
a scrub resistant ink disposed in the ink reservoir, the ink as described in claim 1.

8. A method for forming a scrub-resistant ink composition pursuant to claim 1, comprising:
providing a marking effective amount of a dye suitable for use in marking skin; mixing the dye with a first solvent comprising 50% to 90% of a polar aprotic solvent, wherein the dye is 1 to 5 percent of the resultant ink composition; and obtaining the ink composition.

9. The method of claim 8, wherein the first solvent comprises dimethyl sulfoxide (DMSO).

10. The method of claim 8, wherein the dye comprises Gentian violet.

11. The method of claim 8, wherein providing the marking effective amount of the dye comprises:
mixing a marking effective amount of the dye with a second solvent to form a dye concentrate prior to mixing the dye concentrate with the first solvent to form the ink.

12. The method of claim 8, wherein providing the marking effective amount of the dye comprises:
providing a pre-existing ink solution having the marking effective amount of the dye contained therein; and
wherein mixing the dye with the first solvent comprises mixing the first solvent into the pre-existing ink to form an ink mixture having a resultant composition of 50 to 90 percent of the first solvent.

13. The ink composition of claim 1, wherein the composition is free of alcohol.

14. The ink composition of claim 1, wherein the solvent comprises about 60% to about 90% of the polar aprotic solvent(s).

15. The ink composition of claim 14, wherein polar aprotic solvent, water and dye comprise 98% or more of the ink composition.

16. The ink composition of claim 1, wherein the solvent comprises about 65% to about 85% of the polar aprotic solvent(s).

17. The ink composition of claim 1, wherein the ink if applied to human skin resists smearing when scrubbed for 30 seconds with a 2 percent w/w solution of chlorhexidine in 70 percent by volume isopropyl alcohol mixed with water.

* * * * *